United States Patent [19]

Green

[11] Patent Number: 5,453,274
[45] Date of Patent: Sep. 26, 1995

[54] HOT PEPPER PAPER

[76] Inventor: Olive P. Green, 14019 Beach Blvd. #995, Jacksonville Beach, Fla. 32250-1557

[21] Appl. No.: 316,225

[22] Filed: Sep. 30, 1994

[51] Int. Cl.[6] .................................................. A01N 25/34
[52] U.S. Cl. ......................... 424/403; 424/407; 514/918; 514/919
[58] Field of Search ................................. 424/403, 407; 106/15.05; 514/918, 919

[56] References Cited

U.S. PATENT DOCUMENTS

| | | | |
|---|---|---|---|
| 2,980,941 | 12/1958 | Miller. | |
| 3,310,235 | 3/1962 | Zbinden | 360/30.2 |
| 3,343,664 | 9/1967 | Poitras | 128/272 |
| 3,623,659 | 11/1971 | Maierson et al. | 252/316 |
| 4,820,517 | 4/1989 | Pfeiffer et al. | 424/407 |
| 5,142,817 | 9/1992 | Rolf | 106/15.05 |

Primary Examiner—Thurman K. Page
Assistant Examiner—Pamela S. Webber

[57] ABSTRACT

A hot pepper paper system comprising a sheet of paper in a rectangular configuration having long front and rear edges and having short side edges therebetween. The sheet of paper has a front side and a back side. Further included is a layer of an insect repelling material on the front side of the paper.

1 Claim, 3 Drawing Sheets

1
HOT PEPPER PAPER

BACKGROUND OF THE INVENTION

1. Field of the Invention

The present invention relates to hot pepper paper and more particularly pertains to ridding areas of ants or like pests through use of hot pepper in areas to be controlled.

2. Description of the Prior Art

The use of bug repellents and pesticides of a wide variety of formulations and designs is known in the prior art. More specifically, bug repellents and pesticides of a wide variety of formulations and designs heretofore devised and utilized fox, the purpose of removing insects or other pests from any area of habitation through a wide variety of methods, materials and apparatuses are known to consist basically of familiar, expected and obvious structural configurations, notwithstanding the myriad of designs encompassed by the crowded prior art which have been developed for the fulfillment of countless objectives and requirements.

By way of example, the prior art discloses in U.S. Pat. No. 4,820,517 to Pfeiffer et al a process for obtaining a pepper extract with insecticidal activity.

U.S. Pat. No. 5,042,192 to Osteen discloses a support and consumables support with barrier container.

U.S. Pat. No. 5,109,800 to Williams discloses an insect barrier stand.

U.S. Pat. No. 5,148,626 to Haake, Sr., discloses an insect barrier and deterrent device.

Lastly, U.S. Pat. No. 5,258,408 to Steltenkamp discloses a process of repelling insects from an area by application of N-Alkyl neoalkanamide insect repellent thereto.

In this respect, the hot pepper paper according to the present invention substantially departs from the conventional concepts and designs of the prior art, and in so doing provides an apparatus primarily developed for the purpose of ridding areas of ants or like pests through use of hot pepper in areas to be controlled.

Therefore, it can be appreciated that there exists a continuing need for new and improved hot pepper paper which can be used to rid areas of ants or like pests through use of hot pepper in areas to be controlled. In this regard, the present invention substantially fulfills this need.

SUMMARY OF THE INVENTION

In view of the foregoing disadvantages inherent in the known types of bug repellents and pesticides of a wide variety of formulations and designs now present in the prior art, the present invention provides an improved hot pepper paper. As such, the general purpose of the present invention, which will be described subsequently in greater detail, is to provide a new and improved hot pepper paper apparatus and method which has all the advantages of the prior art and none of the disadvantages.

To attain this, the present invention essentially comprises a new and improved hot pepper paper system comprising, in combination, a paper sheet in a rectangular configuration having long front and rear edges and having short side edges therebetween. The sheet of paper has a front face and a back face. Further included is a backing sheet of an adhesive protective film in a rectangular configuration. The backing sheet has long front and rear edges and short side edges configured to be essentially coextensive with that of the paper sheet. The backing sheet has a front face and a back face which are coupled to the back face of the paper sheet. A pressure sensitive adhesive couples the back face of the paper sheet and the front face of the backing sheet. The backing sheet adapts to be peeled from the adhesive to allow adhesively securing of the paper sheet to a recipient surface through the adhesive upon the removal of the backing sheet. Further included is a layer of an insect repelling material on the front side of the paper. The repellent material is in a rectangular configuration having long front and rear edges and short side edges to create a rectangular insect repelling surface similar in shape to the front surface of the paper but of a reduced size with a small border of paper therearound. The repellent material is fabricated of ground particles of pepper and an adhesive liquid dried on the front face of the paper with the particles of pepper embedded therein.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and An even further object of the present invention is to provide a new and improved hot pepper paper which is susceptible of a low cost of manufacture with regard to both materials and labor, and which accordingly is then susceptible of low prices of sale to the consuming public, thereby making such bug repellents and pesticides of a wide variety of formulations and designs economically available to the buying public.

Still yet another object of the present invention is to provide a new and improved hot pepper paper which provides in the apparatuses and methods of the prior art some of the advantages thereof, while simultaneously overcoming some of the disadvantages normally associated therewith.

Still another object of the present invention is to rid areas of ants or like pests through use of hot pepper in areas to be controlled.

Lastly, it is an object of the present invention to provide a new and improved hot pepper paper system comprising a sheet of paper in a rectangular configuration having long front and rear edges and having short side edges therebetween. The practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hot pepper paper which has all the advantages of the prior art bug repellents and pesticides of a wide variety of formulations and designs and none of the disadvantages.

It is another object of the present invention to provide a new and improved hot pepper paper which may be easily and efficiently manufactured and marketed.

It is a further object of the present invention to provide a new and improved hot pepper paper which is of a durable and reliable construction. sheet of paper has a front side and a back side. Further included is a layer of an insect repelling material on the front side of the paper.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
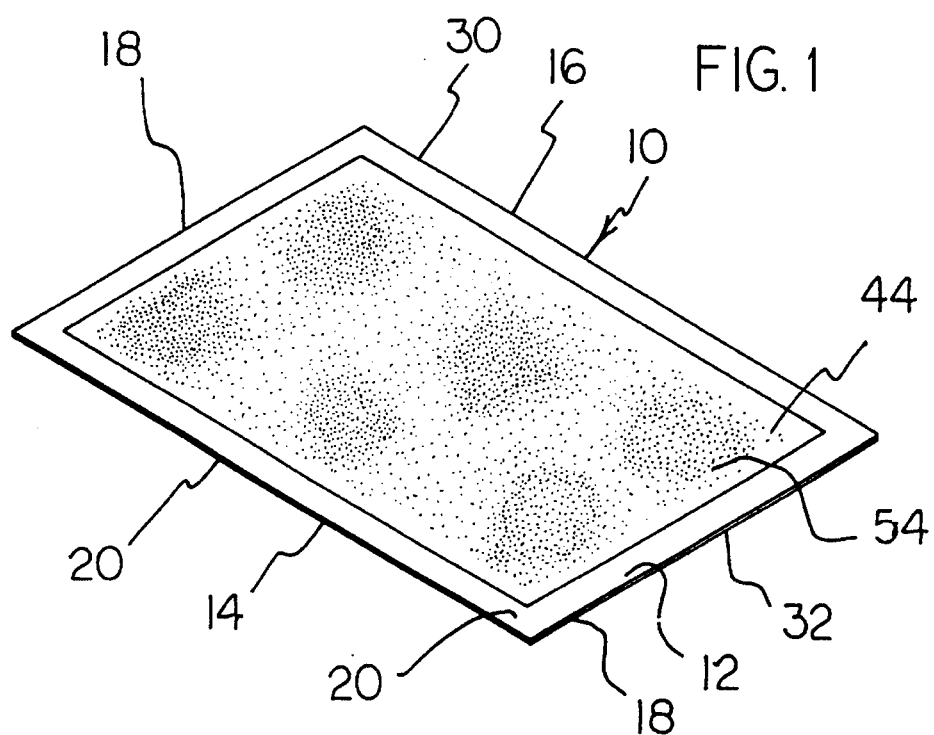
FIG. 1 is a perspective illustration of the preferred embodiment of the hot pepper paper constructed in accordance with the principles of the present invention.
Figure 2:
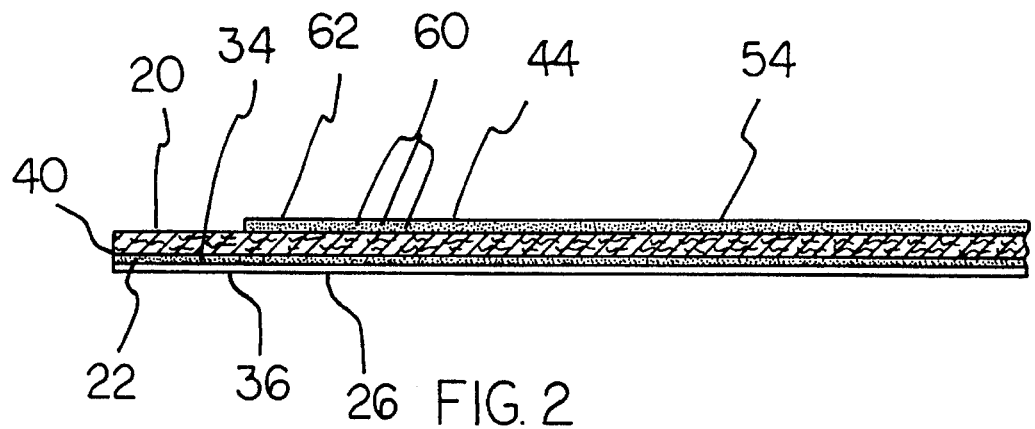
FIG. 2 is a cross-sectional view of the device shown in FIG. 1.

With reference now to the drawings, and in particular to FIG. 1 thereof, a new and improved hot pepper paper embodying the principles and concepts of the present invention and generally designated by the reference numeral 10 will be described.

The present invention, the new and improved hot pepper paper, is comprised of a plurality of components. Such components in their broadest context include a paper sheet, a backing sheet, an adhesive and an insect repelling material. Such components are individually configured and correlated with respect to each other so as to attain the desired objective.

The primary component of the system 10 of the present invention is a paper sheet 12. Such sheet is in a rectangular configuration. It has long front and rear edges 14, 16. It also has parallel short edges 18 between the front and rear edges. The sheet of paper has a front face 20 as well as a back face 22.

Next provided is a backing sheet 26. Such sheet is of an adhesive film, preferably plastic, in a rectangular configuration. The backing sheet has long front and rear edges, 28, 30 parallel with each other. It also has short side edges 32 between the front and rear edges. The backing sheet is configured to be essentially coextensive with the paper sheet. The backing sheet has a front face 34 and a back face 36. The backing sheet is adapted to be coupled to the back face of the paper sheet.

Next provided is a pressure sensitive adhesive 40. Such adhesive is between and couples the back face of the paper sheet and the front face of the backing sheet. The backing sheet is adapted to be peeled from the adhesive to allow the adhesive to secure the paper sheet to a recipient surface whereat the insects are to be controlled. Such securing is through the adhesive as occurs following the removal of the backing sheet therefrom.

Next provided is a layer of insect repelling material 44. Such material is located on the front side of the paper. The repellent material is preferably formed in a rectangular configuration. Such configuration has long front and rear edges 44, 46. It also has short side edges 50. This creates a rectangular insect repelling surface 52. It is similar in shape to the front surface of the paper. It is, however, of a reduced size. This generates a small border 54 of paper therearound.

The repellent material is preferably fabricated of ground particles of pepper 58, a substance from which ants and other insects will depart. In association with the pepper particles, an adhesive liquid 60 is dried on the front surface of the paper. When so drying, particles of pepper therein will become embedded to form the insect repelling material.

Figure 3:
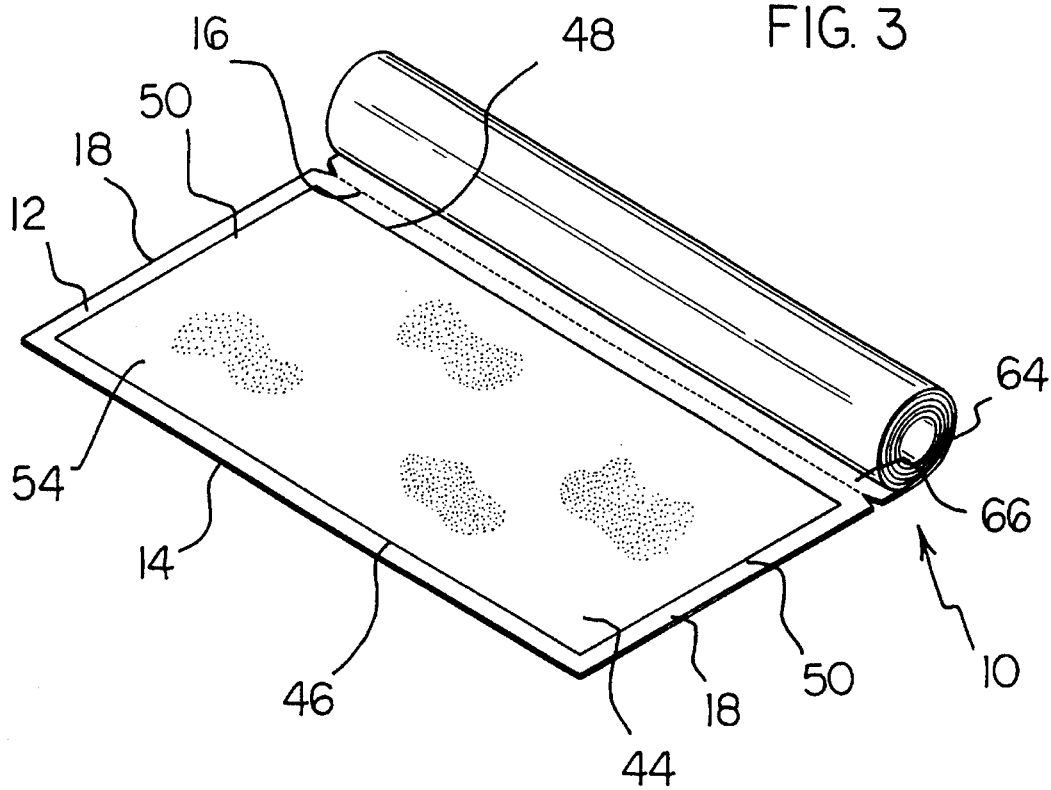
FIG. 3 is a perspective illustration of the device shown in FIGS. 1 and 2 but illustrating the individual sheets in roll form adapted to be separated individually from the roll.
Figure 4:
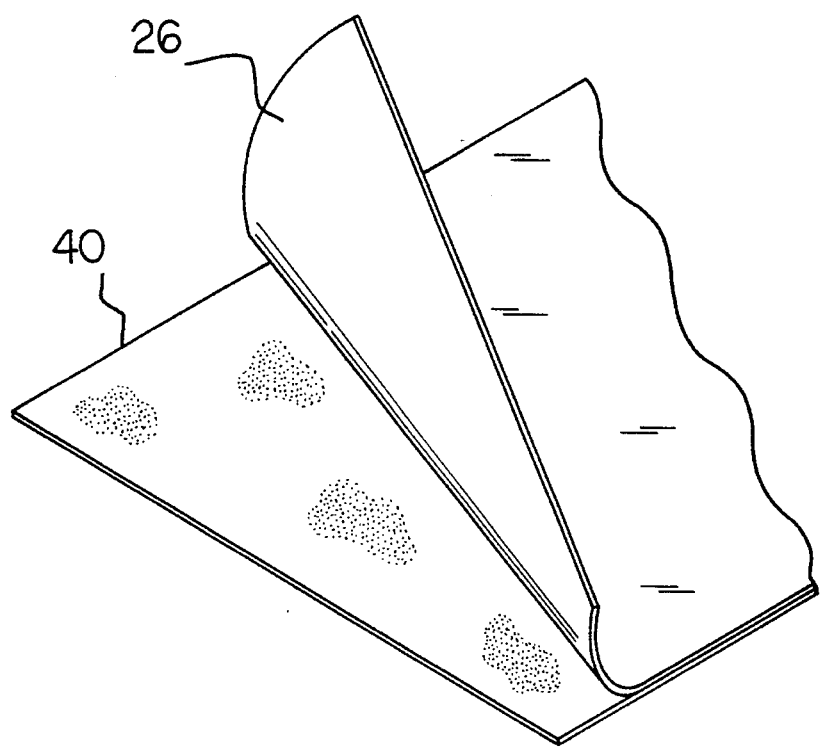
FIG. 4 is a perspective showing of one of the devices with the protective film partially peeled therefrom.

Next provided is a plurality of similar sheets 12 with adhesive, backing sheet and insect repelling material. Such plurality of sheets are formed in the configuration of a roll 64. Note FIG. 3. In association therewith, serrations 66 are formed in a line between the rear edge of the trailing edge of the sheet to be used and the leading edge of the next sheet to be used. The serration line facilitates the separation of one sheet from the next for appropriate use.

Figure 5:
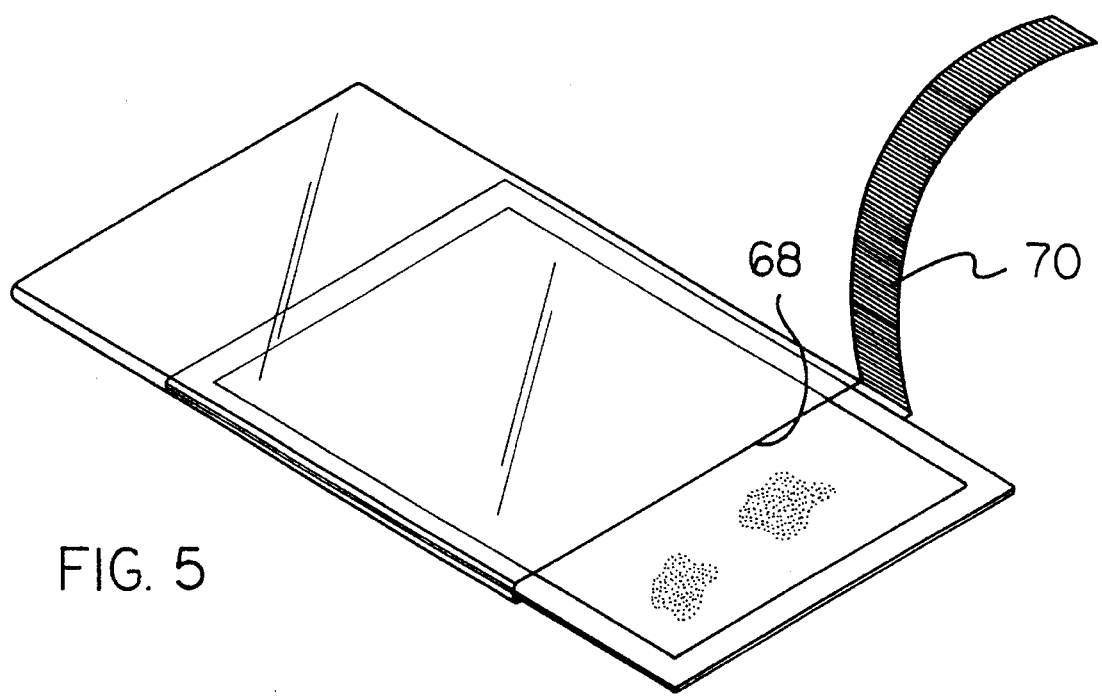
FIG. 5 is a perspective illustration showing a sheet of the device of the prior Figures as it is wrapped and partially removed.

FIG. 5 shows an alternate embodiment of the invention wherein the sheets are separately formed and packaged rather than being positioned on a roll. In such situation, each individual sheet is encompassed and encased in a sheet of plastic material 68. A strip 70 is formed in the covering sheet to allow removal of the covering sheet so that the sheet of paper with its associated components may be readily utilized.

Figure 6:
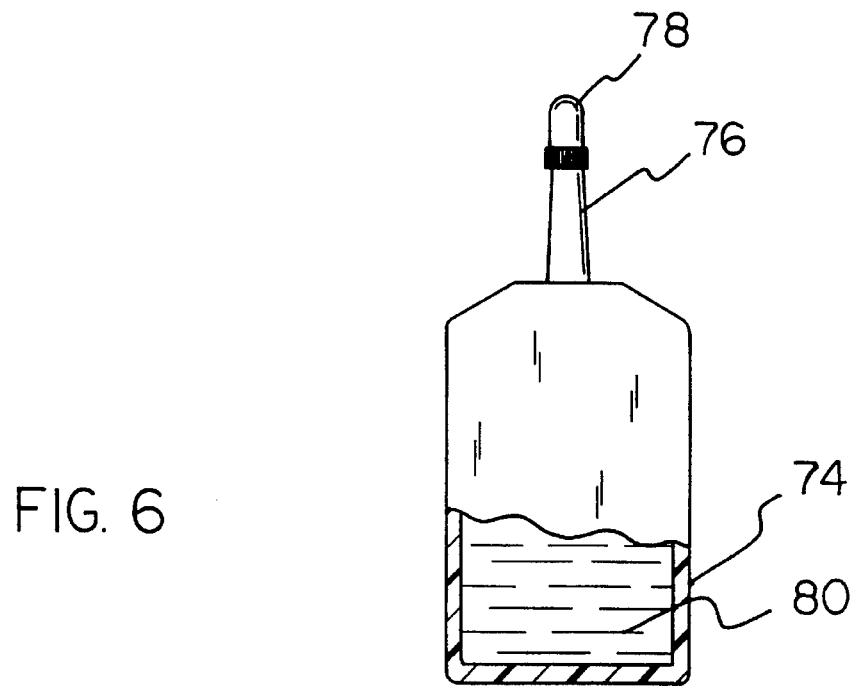
FIG. 6 is a container with a quantity of the fluid used to coat the material to create the device of the prior Figures.

A last embodiment of the invention is shown in FIG. 6. In such embodiment, a bottle 74 is provided of an adhesive to be dried and solidified upon exposure to air. Such bottle 74 has a spout 76 from which a liquid is dispensed. A cap 78 covers the spout when not in use to preclude premature drying. Within the bottle is the adhesive liquid 80 adapted to be dispensed whereafter particles of pepper may be disseminated through the adhesive liquid for being dried while embedded therein.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A hot pepper paper system comprising, in combination:

a paper sheet in a rectangular configuration having long front and rear edges and having short side edges therebetween, the sheet of paper having a front face and a back face;

a backing sheet of an adhesive protective film in a rectangular configuration, the backing sheet having long front and rear edges and short side edges configured to be essentially coextensive with that of the paper sheet, the backing sheet having a front face and a back face being coupled to the back face of the paper sheet;

a pressure sensitive adhesive coupling the back face of the paper sheet and the front face of the backing sheet, the backing sheet adapted to be peeled from the adhesive to allow adhesively securing of the paper sheet to a recipient surface through the adhesive upon the removal of the backing sheet;

a layer of an insect repelling material on the front side of the paper, the repellent material being in a rectangular configuration having long front and rear edges and short side edges to create a rectangular insect repelling surface similar in shape to the front surface of the paper but of a reduced size with a small border of paper therearound, the repellent material being fabricated of ground particles of pepper and an adhesive liquid dried on the front face of the paper with the particles of pepper embedded therein; and a shell of protective plastic material in a rectangular configuration adapted for removable coupling of the paper therein, the plastic material having a strip formed therein for removal of the paper therefrom.

* * * * *